United States Patent [19]

Shigematsu et al.

[11] Patent Number: 4,832,729
[45] Date of Patent: May 23, 1989

[54] PICOLINIC ACID DERIVATIVES AND HERBICIDAL COMPOSITIONS

[75] Inventors: Masahiro Shigematsu; Hideo Ohi, both of Shizuoka; Shoji Kusano, Hamamatsu; Takeshige Miyazawa, Shizuoka; Satoru Takahashi, Shizuoka; Yasuhumi Toyokawa, Shizuoka; Ikuo Kajiwara, Nagaokakyo, all of Japan

[73] Assignees: Kumiai Chemical Industry Co., Ltd.; Ihara Chemical Industry Co., Ltd., both of Tokyo, Japan

[21] Appl. No.: 37,322

[22] Filed: Apr. 13, 1987

[30] Foreign Application Priority Data

Jun. 14, 1986 [JP] Japan ................... 61-138702
Feb. 12, 1987 [JP] Japan ................... 62-30588

[51] Int. Cl.⁴ .................... A01N 43/48; C07D 401/12
[52] U.S. Cl. ........................... 71/92; 544/225; 544/300; 544/310; 544/316
[58] Field of Search ............... 544/300, 310, 316, 225; 71/92

[56] References Cited

U.S. PATENT DOCUMENTS 4,427,437 1/1978 Serban et al. ................... 71/92

FOREIGN PATENT DOCUMENTS 0082244 6/1983 European Pat. Off. .
9474 5/1967 Japan .
117486 9/1979 Japan .

OTHER PUBLICATIONS

Chemical Abstracts, vol. 93, No. 15, Oct. 13, 1980, Columbus, Ohio, USA Kijima, Teruomi; Oto, Takao (Sankyo Co., Ltd.) "2-Phenoxypyrimidine derivatives" p. 722, column 1, abstract-No. 150-268c & Jpn. Kokai Tokkyo Koho 79 117 486.
Chemical Abstracts; vol. 95, No. 7, Aug. 17, 1981, Columbus, Ohio USA Jojima, Teruomi; Takeshiba, Hideo; Kinoto, Takao; Kondo, Yasuhiko.
"Regioselective sysnthesis of 4-aryloxy-2-chloropyrimidines and their herbicidal activity" p. 713, column 2, abstract-No. 62 115m & Sankyo Kenkyusho Nempo 1980, 32, 114-20.
"Syntheses and Herbicidal Activities of Phenoxypyrimidines and Phenoxytriazines", Agr. Biol. Chem. vol. 30, No. 9, pp. 896-905, 1966.

*Primary Examiner*—Donald G. Daus
*Assistant Examiner*—Cecilia Shen
*Attorney, Agent, or Firm*—Oblon, Fisher, Spivak, McClelland & Maier

[57] ABSTRACT

A picolinic acid derivative having the formula:

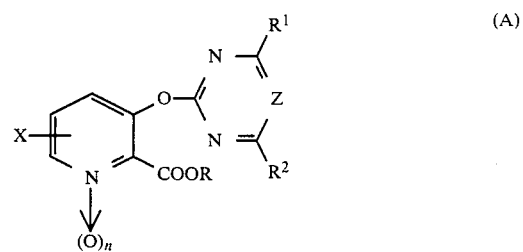

wherein R is a hydrogen atom, an alkyl group, an alkenyl group, an alkynyl group, an alkali metal atom, an alkaline earth metal atom, an alkylammonium group or

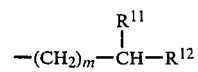

[wherein $R^{11}$ is a hydrogen atom or an alkyl group, $R^{12}$ is an alkoxycarbonyl group, a cyano group, a halogen atom, an acetyl group, a pivaloyl group, a benzoyl group, an alkoxy group, a phenoxy group, a halogenoacetyloxy group, a methylsulfonyloxy group, a hydroxyl group, an alkylthio group, an alkylsulfonyl group, a phenylthio group, a dialkylamino group, a naphthyl group, a pyridyl group,

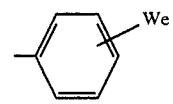

(wherein W is a hydrogen atom, a halogen atom, an alkyl group, an alkoxy group, a phenoxy group, a nitro group or an alkoxycarbonyl group, and e is 1 or 2) or

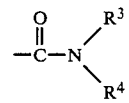

(wherein each of $R^3$ and $R^4$ which may be the same or different, is a hydrogen atom, an alkyl group, an alkenyl group or a phenyl group), and m is an integer of from 0 to 2], each of $R^1$ and $R^2$ which may be the same or different, is a halogen atom, a lower alkyl group, a lower alkoxy group or a lower haloalkoxy group, X is a hydrogen atom, a halogen atom or a lower alkyl group, Z is a methine group or a nitrogen atom, and n is 0 or 1, or a salt thereof.

35 Claims, No Drawings

PICOLINIC ACID DERIVATIVES AND HERBICIDAL COMPOSITIONS

The present invention relates to novel picolinic acid derivatives, processes for their production, herbicidal compositions containing them, and a herbicidal method for applying them.

Some 2-phenoxy-5-chloropyrimidine derivatives have been known as herbicides [Japanese Unexamined Patent Publication No. 55729/1979, and Agr. Biol. Chem., Vol. 30, No. 9, p.896 (1966)].

However, such compounds have a drawback that their herbicidal activities against perennial weeds are poor. In recent years, a number of herbicides have been developed and practically used, and they have contributed to the saving of energy for the agricultural operations and to the improvement of the production efficiency. However, in their practical use, such herbicides have various problems with respect to the herbicidal effects and the safety to crop plants. For example, perennial weeds such as quackgrass (*Agropyron repens*), johnsongrass (*Sorghum halepense*), etc. are distributed widely in the agricultural fields throughout the world, and it is very difficult to control them. Various herbicides have been used to control these weeds, but none of them are fully satisfactory with respect to the certainty of the herbicidal effects and the safety to crop plants. Therefore, it has been desired to develop an improved herbicide.

The present inventors have conducted extensive research on pyrimidinyloxy or triazinyloxy picolinic acid derivatives with an aim to solve the above-mentioned problems, and as a result, have found that the compounds of the present invention having substituents at 4- and 6-positions of the pyrimidine ring or triazine ring, exhibit excellent herbicidal effects against perennial weeds such as quackgrass and johnsongrass, and at the same time they have a high level of safety to crop plants. The present invention has been accomplished on the basis of these discoveries.

The present invention provides a picolinic acid derivative having the formula:

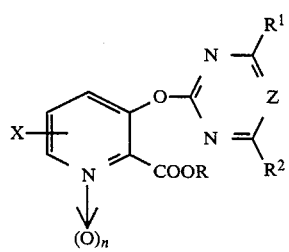
(A)

wherein R is a hydrogen atom, an alkyl group, an alkenyl group, an alkynyl group, an alkali metal atom, an alkaline earth metal atom, an alkylammonium group or

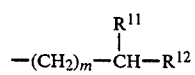

[wherein $R^{11}$ is a hydrogen atom or an alkyl group, $R^{12}$ is an alkoxycarbonyl group, a cyano group, a halogen atom, an acetyl group, a pivaloyl group, a benzoyl group, an alkoxy group, a phenoxy group, a halogenoacetyloxy group, a methylsulfonyloxy group, a hydroxyl group, an alkylthio group, an alkylsulfonyl group, a phenylthio group, a dialkylamino group, a naphthyl group, a pyridyl group,

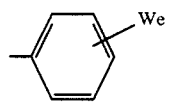

(wherein W is a hydrogen atom, a halogen atom, an alkyl group, an alkoxy group, a phenoxy group, a nitro group or an alkoxycarbonyl group, and e is 1 or 2) or

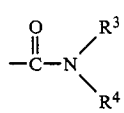

(wherein each of $R^3$ and $R^4$ which may be the same or different, is a hydrogen atom, an alkyl group, an alkenyl group or a phenyl group), and m is an integer of from 0 to 2], each of $R^1$ and $R^2$ which may be the same or different, is a halogen atom, a lower alkyl group, a lower alkoxy group or a lower haloalkoxy group, X is a hydrogen atom, a halogen atom or a lower alkyl group, Z is a methine group or a nitrogen atom, and n is 0 or 1, or a salt thereof. Here, the "salt" therefore is meant for a salt such as a quaternary pyridinium salt.

The picolinic acid derivative of the formula A can be produced by a process which comprises reacting a compound of the formula:

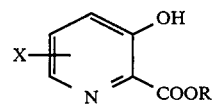
(I)

wherein R and X are as defined above, with a compound of the formula:

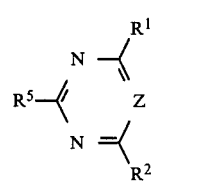
(II)

wherein $R^1$, $R^2$ and Z are defined above, and $R^5$ is a halogen atom or an alkylsulfonyl group, to obtain a compound of the formula:

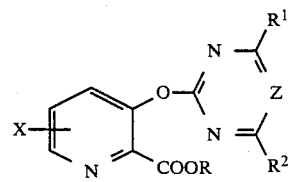
(III)

wherein R, $R^1$, $R^2$, X and Z are defined above; or reacting a compound of the formula III as defined above with a peroxide to obtain a compound of the formula:

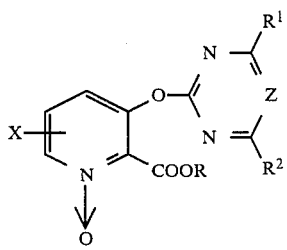

wherein R, $R^1$, $R^2$, X and Z are defined above; or reacting a compound of the formula:

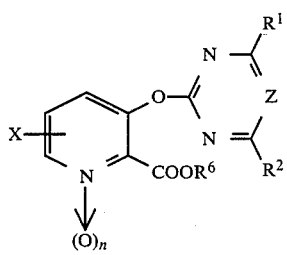

wherein $R^1$, $R^2$, X, Z and n are as defined above, and $R^6$ is a lower alkyl group, with an alkali metal or alkaline earth metal base, to obtain a compound of the formula:

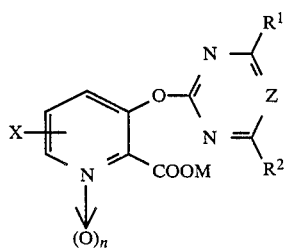

wherein $R^1$, $R^2$, X, Z and n are as defined above, and M is an alkali metal atom or an alkaline earth metal atom; or treating a compound of the formula VI as defined above with an acid to obtain a compound of the formula:

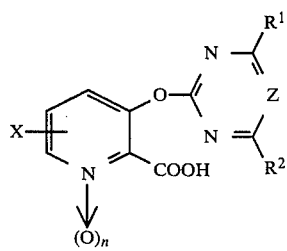

wherein $R^1$, $R^2$, X, Z and n are as defined above; or reacting a compound of the formula:

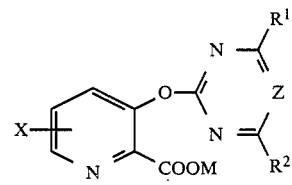

wherein $R^1$, $R^2$, X, Z and M are as defined above, with an alkylating agent of the formula:

$$R-Y \qquad (IX)$$

wherein R is as defined above and Y is a halogen atom, to obtain a compound of the formula III as defined above; or reacting a compound of the formula VII as defined above with a base to obtain a compound of the formula:

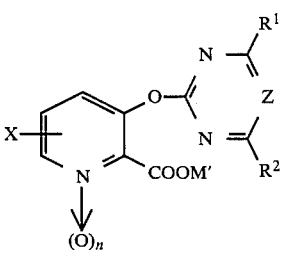

wherein $R^1$, $R^2$, X, Z and n are as defined above, and M' is an alkali metal atom, an alkaline earth metal atom or an organic amine group; or reacting a compound of the formula III with an alkylating agent of the formula:

$$R^7-Y \qquad (XI)$$

wherein $R^7$ is a lower alkyl group, to obtain a compound of the formula:

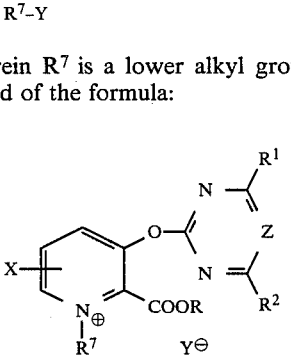

wherein R, $R^1$, $R^2$, $R^7$, X, Z and Y are defined above.

The present invention also provides a herbicidal composition comprising a herbicidally effective amount of a picolinic acid derivative of the formula A or a salt thereof, and an agricultural adjuvant.

Further, the present invention provides a method for killing weeds which comprises applying a herbicidally effective amount of a picolinic acid derivative of the formula A or a salt thereof to a locus to be protected.

Now, the present invention will be described in detail with reference to the preferred embodiments.

Among the compounds of the formula A, preferred are those wherein n is 0 and Z is a methine group. Particularly preferred are those wherein each of $R^1$ and $R^2$ is a lower alkoxy group, particularly a methoxy group, n is 0, Z is a methine group, and X is a hydrogen atom. R is preferably a hydrogen atom, a $C_1$-$C_5$ alkyl group, an unsubstituted benzyl group, a halogen-substituted benzyl group such as a chlorobenzyl group, a lower alkyl-substituted benzyl group, an alkenyl group such as a propenyl group, an alkynyl group such as a propynyl group, a phenethyl group or a methylthiomethyl group.

Now, specific examples of the compound of the present invention will be presented in Table 1. Compound numbers given in the Table will be referred to in the subsequent description in the specification.

TABLE 1

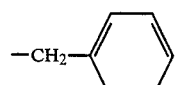

| Compound No. | X | Z | R | $R^1$ | $R^2$ | n | Melting point (°C.) or refractive index $n_D^{20}$ |
|---|---|---|---|---|---|---|---|
| 1 | H | CH | $CH_3$ | $OCH_3$ | $OCH_3$ | 0 | 65–66° C. |
| 2 | " | " | $C_2H_5$ | " | " | 0 | 1.5389 |
| 3 | " | " | $n-C_3H_7$ | " | " | 0 | 1.5328 |
| 4 | " | " | $i-C_3H_7$ | " | " | 0 | 69–70° C. |
| 5 | " | " | $n-C_4H_9$ | " | " | 0 | 1.5320 |
| 6 | " | " | $CH_2=CHCH_2$ | " | " | 0 | 1.5412 |
| 7 | " | " | $-CH_2-C_6H_5$ | " | " | 0 | 1.5725 |
| 8 | " | " | H | " | " | 0 | 120–121° C. |
| 9 | " | " | Na | " | " | 0 | 214–217° C. |
| 10 | " | " | K | " | " | 0 | 232–234° C. |
| 11 | " | " | ½Ca | " | " | 0 | 198–200° C. |
| 12 | " | " | $i-C_3H_7NH_3$ | " | " | 0 | 1.5405 |
| 13 | $6-CH_3$ | " | $CH_3$ | " | " | 0 | 93–96° C. |
| 14 | 5-Cl | " | $CH_3$ | $OCH_3$ | $OCH_3$ | 0 | 1.5560 |
| 15 | H | " | " | $CH_3$ | " | 0 | 1.5408 |
| 16 | " | " | " | " | $CH_3$ | 0 | 1.5510 |
| 17 | " | " | " | $OCH_3$ | $OCHF_2$ | 0 | 1.5240 |
| 18 | " | " | " | " | Cl | 0 | 1.5681 |
| 19 | " | N | " | " | $OCH_3$ | 0 | 100–102° C. |
| 20 | " | CH | $C_{10}H_{21}-n$ | " | " | 0 | 1.5712 |
| 21 | " | " | $-CH_2C\equiv CH$ | " | " | 0 | 83–86° C. |
| 22 | " | " | $-CH_2-C_6H_4-Cl$ (para) | " | " | 0 | 49–52° C. |
| 23 | " | " | $-CH_2-C_6H_4-Cl$ (meta) | " | " | 0 | 63–64° C. |
| 24 | " | " | $-CH_2-C_6H_4-Cl$ (ortho) | " | " | 0 | 1.5830 |
| 25 | " | " | $-CH_2-C_6H_4-CH_3$ | " | " | 0 | 1.5655 |
| 26 | " | " | $-CH_2-C_6H_4-OCH_3$ | " | " | 0 | 1.5679 |

TABLE 1-continued

[Structure: pyridine ring with X substituent, O-C(=N-CR¹)(N=CR²) group, COOR group, and (O)$_n$ on nitrogen]

| Compound No. | X | Z | R | R¹ | R² | n | Melting point (°C.) or refractive index $n_D^{20}$ |
|---|---|---|---|---|---|---|---|
| 27 | " | " | -CH(CH₃)(phenyl) | " | " | 0 | 101–102° C. |
| 28 | " | " | CH₂CH₂(phenyl) | " | " | 0 | 1.5690 |
| 29 | " | " | CH₂(naphthyl) | " | " | 0 | 1.6034 |
| 30 | " | " | CH₂COOCH₃ | " | " | 0 | 1.5435 |
| 31 | " | " | CH₂CH₂CH₂COOC₂H₅ | " | " | 0 | 1.5241 |
| 32 | " | " | -CH(CH₃)COOC₂H₅ | " | " | 0 | 1.5253 |
| 33 | " | " | CH₂CN | " | " | 0 | 1.5530 |
| 34 | " | " | CH₂CH₂CH₂CN | " | " | 0 | 1.5335 |
| 35 | " | " | CH₂CH₂Cl | " | " | 0 | 1.5588 |
| 36 | " | " | CH₂CH₂Br | " | " | 0 | 1.5601 |
| 37 | " | " | CH₂COCH₃ | " | " | 0 | 1.5545 |
| 38 | " | " | CH₂CO-(phenyl) | " | " | 0 | 1.5808 |
| 39 | " | " | CH₂OCH₃ | " | " | 0 | 1.5440 |
| 40 | " | " | CH₂OC₂H₅ | " | " | 0 | 56–58° C. |
| 41 | " | " | CH₂CH₂O-(phenyl) | " | " | 0 | 1.5675 |
| 42 | " | " | CH₂CH₂OH | " | " | 0 | 1.5480 |
| 43 | " | " | CH₂SCH₃ | " | " | 0 | 1.5618 |
| 44 | " | " | CH₂S-(phenyl) | " | " | 0 | 1.5921 |
| 45 | " | " | CH₂SO₂CH₃ | " | " | 0 | Not measurable |

TABLE 1-continued

[Structure: pyridine with X substituent, N-oxide (O)n, ring bearing COOR group and O-linked to a 1,3,5-triazine with R¹ and R² substituents]

| Compound No. | X | Z | R | R¹ | R² | n | Melting point (°C.) or refractive index $n_D^{20}$ |
|---|---|---|---|---|---|---|---|
| 46 | " | " | CH₂CH₂N(CH₃)₂ | " | " | 0 | 1.5378 |
| 47 | " | " | CH₂CON(CH₃)(C₆H₅) | " | " | 0 | 1.5683 |
| 48 | " | " | CH₂CON(CH₂CH=CH₂)₂ | " | " | 0 | 1.5518 |
| 49 | " | " | H | " | " | 1 | 109–114° C. |
| 50 | " | " | CH₃ | " | " | 1 | 137–145° C. |
| 51 | " | " | CH₂-C₆H₅ | " | " | 1 | 133–136° C. |
| 52 | " | " | K | " | " | 1 | 155–175° C. |
| 53 | " | " | -CH₂-(2-CH₃-C₆H₄) | " | " | 0 | 1.5768 |
| 54 | " | " | -CH₂-(3-OCH₃-C₆H₄) | " | " | 0 | 1.5659 |
| 55 | " | " | -CH₂-(2,4-Cl₂-C₆H₃) | " | " | 0 | 61–66° C. |
| 56 | " | " | -CH₂-(3,4-Cl₂-C₆H₃) | " | " | 0 | 1.5840 |
| 57 | " | " | -CH₂-COOC₃H₇-i | " | " | 0 | 85–86° C. |

TABLE 1-continued
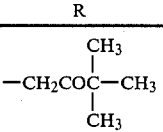
| Compound No. | X | Z | R | R¹ | R² | n | Melting point (°C.) or refractive index $n_D^{20}$ |
|---|---|---|---|---|---|---|---|
| 58 | " | " | —CH$_2$COC(CH$_3$)$_3$ (with three CH$_3$ groups) | " | " | 0 | 123–124° C. |
| 59 | " | " | —CH$_2$CH$_2$OCCHCl$_2$ (with C=O) | " | " | 0 | 1.5370 |
| 60 | " | " | —CH$_2$CH$_2$OS(=O)CH$_3$ | " | " | 0 | 1.5390 |
| 61 | " | " | —CH$_2$-(3-pyridyl) | " | " | 0 | 1.5808 |
| 62 | " | " | —CH$_2$-(3-methylphenyl) | " | " | 0 | 1.5733 |
| 63 | " | " | —CH$_2$-(2-methoxyphenyl) | " | " | 0 | 1.5687 |
| 64 | " | " | —CH$_2$-(3-phenoxyphenyl) | " | " | 0 | 1.5960 |
| 65 | " | " | —CH$_2$-(4-nitrophenyl) | " | " | 0 | 123–130° C. |
| 66 | " | " | —CH$_2$-(3-nitrophenyl) | " | " | 0 | 98–105° C. |

TABLE 1-continued

[Structure: pyridine ring with X substituent, O-C(=N-CR¹=N-CR²=N) triazine group, COOR group, and N→(O)ₙ]

| Compound No. | X | Z | R | R¹ | R² | n | Melting point (°C.) or refractive index $n_D^{20}$ |
|---|---|---|---|---|---|---|---|
| 67 | " | " | −CH₂−C₆H₄(NO₂) (ortho) | " | " | 0 | 125–130° C. |
| 68 | " | " | −CH₂−C₆H₄−Br (para) | " | " | 0 | 68–70° C. |
| 69 | " | " | −CH₂−C₆H₄−Br (meta) | " | " | 0 | 64–70° C. |
| 70 | " | " | −CH₂−C₆H₄−Br (ortho) | " | " | 0 | 82–88° C. |
| 71 | " | " | −CH₂−C₆H₃(Cl)₂ (2,5-dichloro) | " | " | 0 | 144–146° C. |
| 72 | " | " | −CH₂−C₆H₄(COOCH₃) | " | " | 0 | 90–95° C. |
| 73 | " | " | −CH₂CON(C₂H₅)₂ | " | " | 0 | 105–107° C. |
| 74 | " | " | −CH₂CON(C₃H₇−i)₂ | " | " | 0 | 114–115° C. |
| 75 | " | N | −CH₂CON(CH₃)(C₆H₅) | " | " | 0 | 110–115° C. |
| 76 | " | " | −CH₂−C₆H₄−Cl (meta) | " | " | 0 | 120–121° C. |

TABLE 1-continued

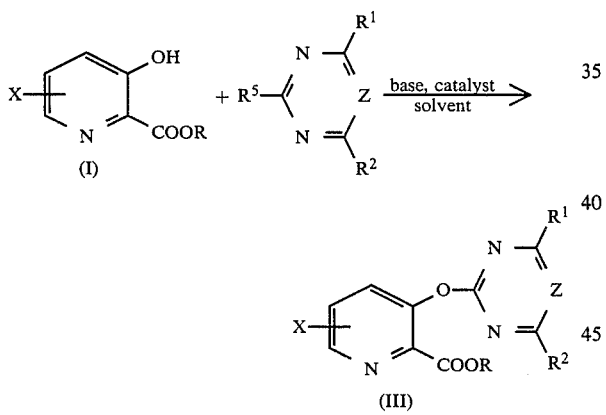

| Compound No. | X | Z | R | R¹ | R² | n | Melting point (°C.) or refractive index $n_D^{20}$ |
|---|---|---|---|---|---|---|---|
| 77 | | (structure shown) | | | | | 115–125° C. |

The compounds of the present invention can be produced by the following processes A to F, but the production is not restricted to such processes.

PROCESS A

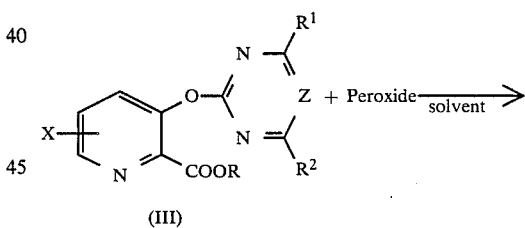

In the above formulas, X, Z, R, R¹ and R² are as defined above, and R⁵ is a halogen atom or an alkylsulfonyl group.

The compounds of the formula III of the present invention can be produced by reacting the compound of the formula I with a pyrimidine derivative of the formula II in the presence of a base, preferably in an inert solvent, within a temperature range of from room temperature to the boiling point of the solvent for from a few minutes to a few hours. In the case where R⁵ is an alkylsulfonyl group, it is preferred to add a halogenated alkali metal such as potassium iodide, or a halogenated alkaline earth metal or a halogenated transition metal, as a catalyst. Here, the solvent may be a hydrocarbon solvent such as benzene or toluene, an ester solvent such as methyl acetate or ethyl acetate, a halogenated hydrocarbon solvent such as dichloromethane or chloroform, an ether solvent such as tetrahydrofuran or 1,4-dioxane, a ketone solvent such as acetone or methyl ethyl ketone, an aprotic polar solvent such as dimethylformamide or dimethylacetamide, or acetonitrile. The base may be an alkali metal such as sodium metal or potassium metal, an alkali metal hydride or alkaline earth metal hydride such as sodium hydride, potassium hydride or calcium hydride, a carbonate such as sodium carbonate, potassium carbonate or calcium carbonate, or a metal hydroxide such as potassium hydroxide or calcium hydroxide.

PROCESS B

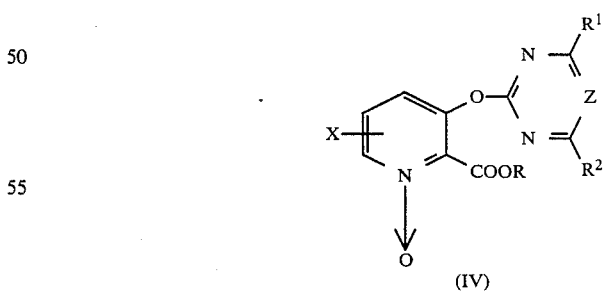

In the above formulas, X, Z, R, R¹ and R² are as defined above.

Among the compounds of the present invention, those represented by the formula IV can be produced by reacting the compound of the formula III with a peroxide in an inert solvent within a temperature range of from room temperature to the boiling point of the solvent for from a few minutes to a few tens hours. Here, as the peroxide, an organic peroxide such as m- chloroperbenzoic acid or t-butylhydroperoxide, or hydrogen peroxide, may be employed. As the solvent, a halogenated hydrocarbon such as dichloromethane or chloroform, an alcohol solvent such as methanol or ethanol, acetic acid or water, may be employed.

PROCESS C

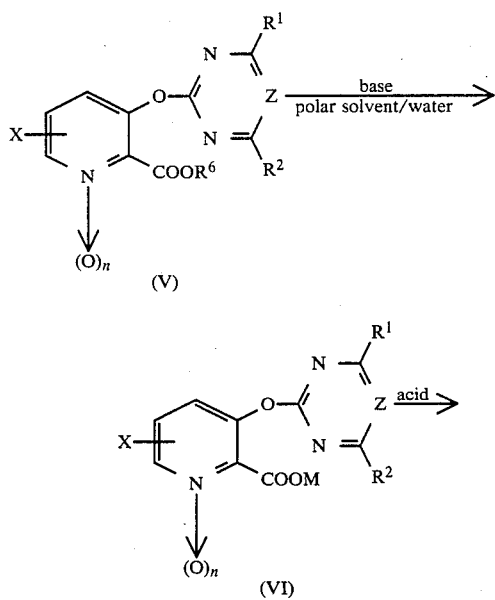

In the above formulas, X, Z, $R^1$ and $R^2$ are as defined above, $R^6$ is a lower alkyl group, M is an alkali metal atom or an alkaline earth metal atom, and n is 0 or 1.

Among the compounds of the present invention, those represented by the formula VI can be produced by reacting the compound of the formula V in the presence of a base in a polar solvent or water, or in a solvent mixture of a polar solvent and water, within a temperature range of from room temperature to the boiling point of the solvent for from a few hours to a few tens hours. The compounds of the formula VII can be obtained by treating the compounds of the formula VI with an acid for precipitation.

As the solvent, an alcohol solvent such as methanol or ethanol, an ether polar solvent such as 1,4-dioxane or tetrahydrofuran, or an amide polar solvent such as dimethylformamide or dimethylacetamide, may be employed. However, the solvent is not restricted to such specific examples.

As the base, a carbonate such as sodium carbonate, potassium carbonate or calcium carbonate, or a metal hydroxide such as sodium hydroxide, potassium hydroxide or calcium hydroxide, may be used. The compound of the formula VI may take the form of a hydrate.

PROCESS D

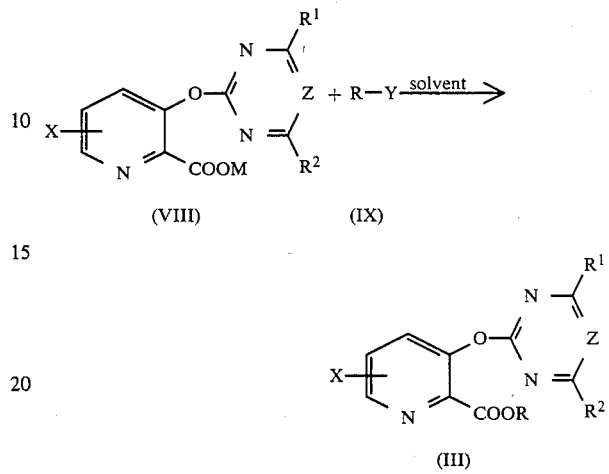

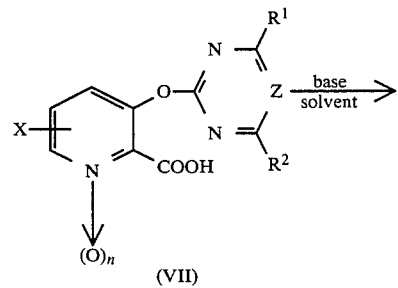

In the above formulas, X, Z, R, $R^1$, $R^2$ and M are as defined above, and Y is a halogen atom.

Among the compounds of the present invention, those represented by the formula III can be produced by reacting a compound of the formula VIII with an alkylating agent of the formula IX, preferably in an inert solvent, within a temperature range of from room temperature to the boiling point of the solvent for from a few minutes to a few hours. Here, the solvent may be the same as used for the Process A as described above.

PROCESS E

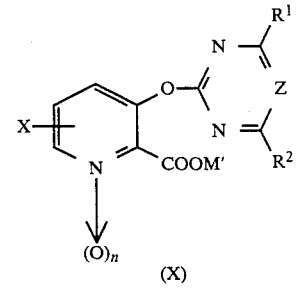

In the above formulas, X, Z, $R^1$, $R^2$ and n are as defined above, and M' is a cation such as an alkali metal, an alkaline earth metal or an organic amine.

Among the compounds of the present invention, those represented by the formula X can be produced by reacting the compound of the formula VII with a base in the presence or absence of a solvent, within a temperature range of from room temperature to the boiling point of the solvent for from a few minutes to a few hours. Here, the solvent may be the same as used in the Process A as described above, and an alcohol such as methanol or ethanol and water may also be employed. Likewise, the base may be the same base as used in the Process A. As the organic base, ammonia, an alkylamine (primary amine) a dialkylamine (secondary amine) or a trialkylamine (tertiary amine) may be used. The compound of the formula X may take the form of a hydrate.

PROCESS F

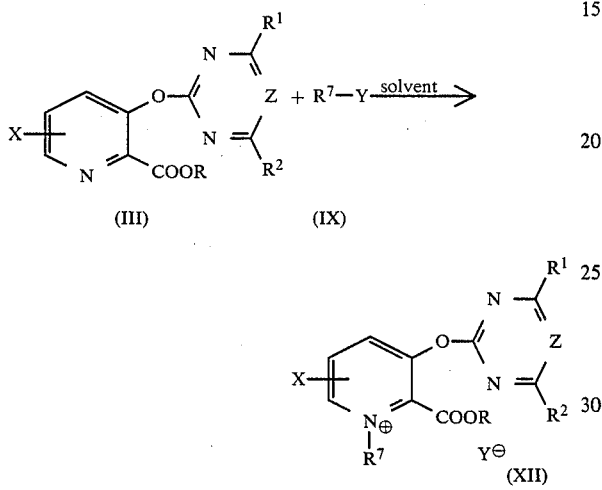

In the above formulas, X, Z, R, $R^1$, $R^2$ and Y are as defined above, and $R^7$ is a lower alkyl group.

Among the compounds of the present invention, those represented by the formula XII can be produced by reacting the compound of the formula III with an alkylating agent of the formula XI in the absence of a solvent or in the same solvent as used in the Process A, within a temperature range of from room temperature to the boiling point of the solvent for from a few hours to a few ten hours. The compound of the formula XII may take the form of a hydrate.

Now, the present invention will be described in further detail with reference to Examples. However, it should be understood that the present invention is by no means restricted to such specific Examples.

EXAMPLE 1

Preparation of methyl 3-(4,6-dimethoxypyrimidin-2-yl)oxy picolinate (Compound No. 1)

To a solution of 30.0 g of methyl 3-hydroxypicolinate in 250 ml of dimethylformamide, 42.7 g of 4,6-dimethoxy-2-methylsulfonylpyrimidine, 32.5 g of potassium carbonate and 16.3 g of potassium iodide, were added, and the mixture was heated and stirred at a reaction temperature of from 100° to 110° C. for 1.5 hours. After cooling, the reaction solution was poured into water, and extracted with ethyl acetate. The extract was washed with water, and dried over magnesium sulfate. Ethyl acetate was distilled off under reduced pressure, and the residue was recrystallized from a solvent mixture of hexane, diisopropyl ether and toluene, to obtain 37.2 g of methyl 3-(4,6-dimethoxypyrimidin-2-yl)oxy picolinate. (Yield: 65%, white crystal, melting point: 65°–66° C.)

EXAMPLE 2

Preparation of ethyl 3-(4,6-dimethoxypyrimidin-2-yl)oxy picolinate (Compound No. 2)

To 0.5 g of 60% sodium hydride, 50 ml of hexane was added, and subjected to decantation. Then, the mixture was suspended in 30 ml of dimethylformamide. To the dimethylformamide suspension, 1.9 g of ethyl 3-hydroxypicolinate was gradually added, and the 2.0 g of 2-chloro-4,6-dimethoxypyrimidine was added. The mixture was heated and stirred at a reaction temperature of from 130° to 140° C. for 4 hours. After cooling, the reaction solution was poured into water, and extracted with ethyl acetate. The extract was washed with water and dried over magnesium sulfate. Ethyl acetate was distilled off under reduced pressure, and the residue was purified by silica gel column chromatography (hexane-ethyl acetate) to obtain 1.4 g of ethyl 3-(4,6-dimethoxypyrimidin-2-yl)oxy picolinate. (Yield: 40%, pale yellow liquid, refractive index $n_D^{20} = 1.5389$)

EXAMPLE 3

Preparation of potassium 3-(4,6-dimethoxypyrimidin-2-yl)oxy picolinate (Compound No. 10)

To a solution of 1.4 g of 85% potassium hydroxide in a mixture of 50 ml of methanol and 1 ml of water, 6.0 g of methyl 3-(4,6-dimethoxypyrimidin-2-yl)oxy picolinate was added, and the mixture was stirred at room temperature for 40 hours. Methanol was distilled off under reduced pressure, and the residue was washed with acetone to obtain 5.9 g of potassium 3-(4,6-dimethoxypyrimidin-2-yl)oxy picolinate mono hydrate. (Yield: 86%, white crystal, melting point: 232°–234° C., thermally decomposed)

EXAMPLE 4

Preparation of 3-(4,6-dimethoxypyrimidin-2-yl)oxy picolinic acid (Compound No. 8)

Concentrated hydrochloric acid was added to 30 ml of an aqueous solution containing 5.9 g of potassium 3-(4,6-dimethoxypyrimidin-2-yl)oxy picolinate monohydrate for acid precipitation, and then extracted with ethyl acetate. The ethyl acetate solution was washed with water, and dried over magnesium sulfate. Then, ethyl acetate was distilled off under reduced pressure, and the residue was washed with diisopropyl ether to obtain 4.0 g of 3-(4,6-dimethoxypyrimidin-2-yl)oxy picolinic acid. (Yield: 82%, white crystal, melting point: 120°–121° C.)

EXAMPLE 5

Preparation of bezyl 3-(4,6-dimethoxypyrimidin-2-yl)oxy picolinate (Compound No. 7)

To a suspension of 0.9 g of potassium 3-(4,6-dimethoxypyrimidin-2-yl)oxy picolinate monohydrate in 20 ml of dimethylformamide, 0.3 g of benzyl chloride was added, and the mixture was heated and stirred at a reaction temperature of from 100° to 110° C. for 1 hour. After cooling, the reaction solution was poured into water, and extracted with ethyl acetate. The extract was washed with water, and dried over magnesium sulfate. Then, ethyl acetate was distilled off under reduced pressure, and the residue was purified by silica gel column chromatography (hexane-ethyl acetate) to obtain 0.9 g of benzyl 3-(4,6-dimethoxypyrimidin-2-yl)oxy picolinate. (Yield: 91%, yellow liquid, refractive index $n_D^{20}=1.5725$)

EXAMPLE 6

Preparation of 2'-chloroethyl 3-(4,6-dimethoxypyrimidin-2-yl)oxy picolinate (Compound No. 35)

To a suspension of 2.0 g of potassium 3-(4,6-dimethoxypyrimidin-2-yl)oxy picolinate monohydrate in 40 ml of dimethylformamide, 6.0 g of 1,2-dichloroethane was added, and the mixture was refluxed under heating at a reaction temperature of from 80° to 90° C. for 45 minutes. After cooling, the reaction solution was poured into water, and extracted with ethyl acetate. The extract was washed with water and dried over magnesium sulfate. Then, ethyl acetate was distilled off under reduced pressure to obtain 0.9 g of 2'-chloroethyl 3-(4,6-dimethoxypyrimidin-2-yl)oxy picolinate. (Yield: 44%, pale yellow liquid, refractive index $n_D^{20}=1.5588$)

EXAMPLE 7

Preparation of methylthiomethyl 3-(4,6-dimethoxypyrimidin-2-yl)oxy picolinate (Compound No. 43)

To a suspension of 4.8 g of potassium 3-(4,6-dimethoxypyrimidin-2-yl)oxy picolinate monohydrate in 40 ml of dimethylformamide, 1.4 g of chloromethyl methyl sulfide was added, and the mixture was heated and stirred at a reaction temperature of from 80° to 90° C. for 20 minutes. After cooling, the reaction solution was poured into water, and extracted with ethyl acetate. The extract was washed with water and dried over magnesium sulfate. The, ethyl acetate was distilled off under reduced pressure to obtain 4.3 g of methylthiomethyl 3-(4,6-dimethoxypyrimidin-2-yl)oxy picolinate. (Yield: 89%, orange liquid, refractive index $n_D^{20}=1.5618$)

EXAMPLE 8

Preparation of benzyl 3-(4,6-dimethoxypyrimidin-2-yl)oxy picolinate N-oxide (Compound No. 51)

To a solution of 6.0 g of benzyl 3-(4,6-dimethoxypyrimidin-2-yl)oxy picolinate in 100 ml of chloroform, 4.63 g (70%) of m-chloroperbenzoic acid was added, and the mixture was refluxed under heating for 8 hours. After cooling, the reaction solution was washed with an aqueous sodium hydrogen carbonate solution, and further washed thoroughly with water, and then dried over magnesium sulfate. Chloroform was distilled off under reduced pressure, and the residue was purified by silica gel column chromatography (hexane-ethyl acetate) to obtain 1.3 g of benzyl 3-(4,6-dimethoxypyrimidin-2-yl)oxy picolinate N-oxide. (Yield: 21%, white crystal, melting point: 133°-136° C.)

EXAMPLE 9 preparation of potassium 3-(4,6-dimethoxypyrimidin-2-yl)oxy picolinate N-oxide (Compound No. 52)

To a solution of 0.6 g of 85% potassium hydroxide in a mixture of 50 ml of methanol and 0.5 ml of water, 2.8 g of methyl 3-(4,6-dimethoxypyrimidin-2-yl)oxy picolinate N-oxide was added, and the mixture was stirred at room temperature for 24 hours. Methanol was distilled off under reduced pressure, and the residue was washed with acetone to obtain 2.5 g of potassium 3-(4,6-dimethoxypyrimidin-2-yl)oxy picolinate N-oxide pentahydrate. (Yield: 65%, pale yellow crystal, melting point: 155°-175° C., thermally decomposed)

EXAMPLE 10

Preparation of 3-(4,6-dimethoxypyrimidin-2-yl)oxy picolinic acid N-oxide (Compound No. 49)

Concentrated hydrochloric acid was added under cooling to 20 ml of an aqueous solution containing 2.0 g of potassium 3-(4,6-dimethoxypyrimidin-2-yl)oxy picolinate N-oxide pentahydrate for acid precipitation, and then extracted with a mixture of ethyl acetate and chloroform. The ethyl acetate-chloroform solution mixture was washed with water and dried over magnesium sulfate. Then, low boiling substances were distilled off under reduced pressure, and the residue was washed with a mixture of ethyl acetate and diisopropyl ether to obtain 0.9 g of 3-(4,6-dimethoxypyrimidin-2-yl)oxy picolinic acid N-oxide. (Yield: 65%, pale yellow crystal, melting point: 109°-114° C., thermally decomposed)

EXAMPLE 11

Preparation of 3'-chlorobenzyl 3-(4,6-dimethoxytriazin-2-yl)oxy picolinate (Compound No. 76)

To a solution of 2.4 g of 3'-chlorobenzyl 3-hydroxy picolinate in 40 ml of dimethylformamide, 1.6 g of 2-chloro-4,6-dimethoxytriazine and 1.3 g of potassium carbonate were added, and the mixture was heated and stirred at a reaction temperature of from 90° to 100° C. for 40 minutes. After cooling, the reaction solution was poured into water, and extracted with chloroform. The extract was washed with water and dried over magnesium sulfate. Then, chloroform was distilled off under reduced pressure, and the residue was washed with diisopropyl ether to obtain 2.4 g of 3'-chlorobenzyl 3-(4,6-dimethoxytriazin-2-yl)oxy picolinate. (Yield: 65%, white crystal, melting point: 120°-121° C.)

EXAMPLE 12

Preparation of methyl 3-(4,6-dimethoxypyrimidin-2-yl)oxy picolinate 1-methiodide (Compound No. 77)

To 2.0 g of methyl 3-(4,6-dimethoxypyrimidin-2-yl)oxy picolinate, 20 ml of methyl iodide was added, and the mixture was stirred at room temperature for 24 hours, and further refluxed under heating for 1 hour. After the reaction, methyl iodide was distilled off under reduced pressure, and the residue was washed with a mixture of ethyl acetate and diisopropyl ether to obtain 0.4 g of methyl 3-(4,6-dimethoxypyrimidin-2-yl)oxy picolinate 1-methiodide. (Yield: 13%, yellow crystal, melting point: 115°-125° C.)

EXAMPLE 13

Preparation of 3'-chlorobenzyl 3-(4,6-dimethoxypyrimidin-2-yl)oxy picolinate (Compound No. 23)

To a suspension of 3.5 g of potassium 3-(4,6-dimethoxypyrimidin-2-yl)oxy picolinate monohydrate in 50 ml of dimethylformamide, 1.6 of 3-chlorobenzyl chloride was added, and the mixture was heated and stirred at a reaction temperature of from 80° to 90° C. for 20 minutes. After cooling, the reaction solution was poured into water and extracted with ethyl acetate. The extract was washed with water and dried over magnesium sulfate. Then, ethyl acetate was distilled off under reduced pressure, and the residue was purified with silica gel column chromatography (hexane-ethyl acetate) to obtain 3.5 g of 3'-chlorobenzyl 3-(4,6-dimethoxypyrimidin-2-yl)oxy picolinate. Then, the product was crystallized. (Yield: 87%, white crystal, melting point: 63°-64° C.)

The herbicidal composition of the present invention comprises a herbicidally effective amount of the pyrimidinyl or triazinyl picolinic acid derivative of the present invention, and an agricultural adjuvant.

As the carrier to be used for the formulation, there may be mentioned a solid carrier such as talc, bentonite, clay, kaolin, diatomaceous earth, white carbon, vermiculite, slaked lime, silica sand, ammonium sulfate or urea, or a liquid carrier such as isopropyl alcohol, xylene, cyclohexane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol or gum arabic may be mentioned. In practical use, such a herbicide may be diluted to a suitable concentration before application, or may directly be applied.

The herbicide of the present invention is capable of controlling various weeds in an upland field by soil treatment before or after the emergence of weeds or by foliage treatment. Further, the herbicide is capable of controlling various weeds in a paddy field by irrigated soil treatment before or after the emergence of weeds.

The dose of the active ingredient varies depending upon the field to be treated i.e. whether it is an agricultural field or non-agricultural field, the type of treatment, i.e. whether it is soil treatment or foliage treatment, the crop plants to be protected and the weeds to be killed. However, it is usually within a range of from 0.1 to 1,000 g/10 a, preferably from 1 to 500 g/10 a.

For instance, for foliage treatment for an upland agricultural field, the dose of the active ingredient is usually from 1 to 100 g/10 a, although it depends on the crop plant and weeds to be killed.

The herbicide of the present invention may be used in combination with other herbicides. Examples of such other herbicides will be given below.

2,4-dichlorophenoxy acetic acid,
3,6-dichloro-2-methoxy bezoic acid,
3-isopropyl-1H-2,1,3-benzothiadiazine-(4)-3H-one-2,2-dioxide,
2-(3,5-dichlorophenyl)-2-(2,2,2-trichloroethyl)oxirane,
1-(α,α-dimethylbenzyl)-3-p-tolylurea,
2-chloro-4,6-bisethylamino-1,3,5-triazine,
2-chloro-4-ethylamino-6-isopropylamino-1,3,5-triazine,
2-chloro-4,6-bisisopropylamino-1,3,5-triazine,
2,4-bisethylamino-6-methylthio-1,3,5-triazine,
2,4-bisisopropylamino-6-methylthio-1,3,5-triazine,
methyl α-(4,6-dimethoxypyrimidin-2-yl carbamoylsulfamoyl)-O-toluylate,
1-[2-(2-chloroethoxy)phenylsulfamoyl]-3-(4-methoxy-6-methyl-1,3,5-triazin-2-yl)urea,
2-(1-ethoxyiminobutyl)-5-(2-ethylthiopropyl-3-hydroxycyclohex-2-enone methyl 3-(1-allyloxyaminobutylidene)-6,6-dimethyl-2,4-dioxocyclohexane carboxylate sodium salt,
4-(2,4-dichlorobenzoyl)-1,3-dimethyl-5-pyrazolyl-ptoluenesulfonate,
3-isopropyl-2,1,3-benzothiadiazinone-(4)-2,2-dioxide,
N-(1-ethylpropyl)-3,4-dimethyl-2,6-dinitroaniline,
α-(2-naphtoxy)propionanilide,
N-(phosphonomethyl)glycidylisopropylamine salt,
2-benzothiazol-2-yloxy-N-methylacetanilide,
2-chloro-2', 6'-diethyl-N-(2-propoxyethyl)acetanilide,
2-chloro-2'-ethyl-N-(2-methoxy-1-methyl ethyl)-6'-methylacetanilide,
S-(2-methyl-1-piperidylecarbonylmethyl)-O,O-di-npropyldithiophosphate,
2-methylthio-4-ethylamino-6-isopropylamino-1,3,5-triazine.

Now, Formulation Examples for the herbicidal composition of the present invention will be given. However, it should be understood that the present invention is by no means restricted to these specific Examples. In these Examples, "%" means "% by weight".

FORMULATION EXAMPLE 1 (wettable powder)

10% of Compound No. 16, 0.5% of Emulgen 810 (trademark, Kao Corporation), 0.5% of Demol N (trademark, Kao Corporation), 20.0% of Kunilite 201 (trademark, Kunimine Kogyo K.K.) and 69.0% of Jeeklite CA (tradename, Jeeklite Company Ltd.) were uniformly mixed and pulverized to obtain a wettable powder.

FORMULATION EXAMPLE 2 (emulsifiable concentrate)

30% of Compound No. 24, 20% of cyclohexanone, 11% of polyoxyethylene alkyl aryl ether, 4% of calcium alkylbenzenesulfonate and 35% of methyl naphthalene, were uniformly dissolved to obtain an emulsifiable concentrate.

FORMULATION EXAMPLE 3 (granule)

5% of Compound No. 32, 2% of a sodium salt of a lauryl alcohol-sulfuric acid ester, 5% of sodium lignin sulfonate, 2% of carboxymethyl cellulose and 86% of clay were uniformly mixed and pulverized. To 100 parts by weight of this mixture, 20 parts by weight of water was added, and the mixture was kneaded, and granulated into granules of from 14 to 32 mesh by means of an extrusion granulating machine, followed by drying to obtain granules.

FORMULATION EXAMPLE 4 (dust)

2% of Compound No. 30, 5% of diatomaceous earth and 93% of clay were uniformly mixed and pulverized to obtain a dust.

The compounds of the present invention are capable of effectively controlling annual weeds such as barnyardgrass (*Echinochloa crus-galli*), crabgrass (*Digitaria sanguinalis*), greenfoxtrail (*Setaria viridis*), shattercane (*Sorghum bicolor*), broad leaf signalgrass (*Brachiaria platyphylla*), fall panicum (*Panicum dichotomiflorum*), itchgrass (*Rottoboellia exaltata*), downy brome (*Bromus tectorum*), water foxtail (*Alopecurus aequalis*), annual bluegrass (*Poa annua*), wild oat (*Avena fatua*), italian ryegrass (*Lolium multifluorum*), green smartweed (*Polygonum nodosum*), slender amarauth (*Amaranthus viridis*), lambsquarters (*Chenopodium album*), velvetleaf (*Abtilon theophrasti*), common cocklebur (*Xanthium strumarium*), morningglory (*Ipomoea spp*), chickweed (*Stellaria media*), prickly sida (*Sida spinosa*), sicklepod (*Cassis tora*), great bindweed (*Calystegia hederacea*), wild mustard (*Brassica arvensis*), jimsonweed (*Datura stramonium*), and rice flatsedge (*Cyperus iria*), and perennial weeds such as johnsongrass (*Sorghum halepense*), bermudagrass (*Cynodon dactylon*) and quackgrass (*Agropyron repens*) grown in upland fields. Further, they are capable of effectively controlling annual weeds such as barnyardgrass (*Echinochloa crus-galli*), unbrellaplant (*Cyperus difformis*), monochoria (*Monochoria vaginalis*), bulrush (*Scirpus hotarui*) and *Alisma canaliculatum*, and perennial weeds such as *Cyperus serotinus*, *Satiggaria pygmaea* and *Eleocharis kuroguwai* grown in paddy fields. They have an extremely high level of safety to crop plants such as corn (*Zea mays*). Furthermore, the compounds of the present invention have a feature that as compared with known compounds specifically disclosed in the above-mentioned publications, their herbicidal effects against annual weeds such as barnyardgrass greenfoxtail and smartweed and against perennial weeds such as johnsongrass are remarkably superior.

Now, the herbicidal effects of the compounds of the present invention will be described with reference to Text Examples.

TEST EXAMPLE 1 (Folige Treatment)

In a 600 cm² pot filled with soil, seeds of barnyardgrass, crabgrass, smartweed, slender amarauth, lambsquarters and rice flatsedge were sown and covered with soil of a thickness of from 0.5 to 1 cm. The pot was cultured in a greenhouse at a temperature of from 20 to 25° C. for 2 weeks, and then a predetermined amount of a wettable powder prepared in accordance with Formulation Example 1 was diluted with water, and applied to the foliage at a rate of 100 liters per 10 ares. The evaluation was conducted on 14th day after the treatment with the herbicide. The results were evaluated in accordance with the standards as identified in Table 2 and shown by the index numbers in Table 3a to 3c.

TABLE 2

| Index No. | Herbicidal effects |
| --- | --- |
| 0 | No herbicidal effect |
| 1 | Herbicidal effect: more than 0% and less than 30% |
| 2 | Herbicidal effect: at least 30% and less than 50% |
| 3 | Herbicidal effect: at least 50% and less than 70% |
| 4 | Herbicidal effect: at least 70% and less than 90% |
| 5 | Herbicidal effect: more than 90% |

TABLE 3

| Compound No. | Dose of active ingredient (g/10a) | Herbicidal effects | | | | | |
| --- | --- | --- | --- | --- | --- | --- | --- |
| | | Ech | Dig | Pol | Ama | Che | Cyi |
| 1 | 400 | 5 | 5 | 5 | 5 | 5 | 5 |
| 2 | 400 | 5 | 5 | 5 | 5 | 5 | 5 |
| 3 | 400 | 5 | 5 | 5 | 5 | 5 | 5 |
| 4 | 400 | 5 | 4 | 3 | 5 | 4 | 2 |
| 5 | 400 | 5 | 4 | 4 | 5 | 5 | 5 |
| 6 | 400 | 5 | 5 | 5 | 5 | 4 | 4 |
| 7 | 400 | 5 | 5 | 5 | 5 | 5 | 5 |
| 8 | 400 | 5 | 5 | 5 | 5 | 5 | 5 |
| 9 | 400 | 5 | 5 | 5 | 5 | 5 | 5 |
| 10 | 400 | 5 | 5 | 4 | 5 | 5 | 5 |
| 11 | 400 | 5 | 5 | 5 | 5 | 5 | 5 |
| 12 | 400 | 5 | 5 | 5 | 5 | 5 | 5 |

TABLE 3-continued

| Compound No. | Dose of active ingredient (g/10a) | Herbicidal effects | | | | | |
| --- | --- | --- | --- | --- | --- | --- | --- |
| | | Ech | Dig | Pol | Ama | Che | Cyi |
| 13 | 400 | 4 | 4 | 4 | 5 | 5 | 5 |
| 14 | 400 | 1 | 1 | 3 | 4 | 5 | 3 |
| 15 | 400 | 3 | 1 | 3 | 5 | 5 | 1 |
| 16 | 400 | 1 | 1 | 2 | 4 | 2 | 0 |
| 17 | 400 | 4 | 3 | 5 | 5 | 5 | 3 |
| 18 | 400 | 3 | 5 | 4 | 5 | 5 | 5 |
| 19 | 400 | 5 | 4 | 4 | 5 | 3 | 4 |
| Comparative Compound A | 400 | 0 | 1 | 2 | 2 | 0 | 5 |
| Comparative Compound B | 400 | 1 | 1 | 2 | 1 | 1 | 5 |
| Comparative Compound C | 400 | 1 | 1 | 1 | 1 | 1 | 1 |
| 20 | 400 | 5 | 5 | 5 | 5 | 5 | 5 |
| 21 | 400 | 5 | 5 | 5 | 5 | 5 | 5 |
| 22 | 400 | 5 | 5 | 5 | 5 | 5 | 5 |
| 23 | 400 | 5 | 5 | 5 | 5 | 5 | 5 |
| 24 | 400 | 5 | 5 | 5 | 5 | 5 | 5 |
| 25 | 400 | 5 | 5 | 5 | 5 | 5 | 5 |
| 26 | 400 | 5 | 5 | 5 | 5 | 5 | 5 |
| 27 | 400 | 5 | 5 | 5 | 5 | 5 | 4 |
| 28 | 400 | 5 | 5 | 5 | 5 | 5 | 5 |
| 29 | 400 | 5 | 5 | 5 | 5 | 5 | 5 |
| 30 | 400 | 5 | 5 | 5 | 5 | 5 | 5 |
| 31 | 400 | 5 | 5 | 5 | 5 | 5 | 5 |
| 32 | 400 | 5 | 5 | 5 | 5 | 5 | 5 |
| 33 | 400 | 5 | 5 | 5 | 5 | 5 | 5 |
| 34 | 400 | 5 | 5 | 5 | 5 | 5 | 5 |
| 35 | 400 | 5 | 5 | 5 | 5 | 5 | 5 |
| 36 | 400 | 5 | 5 | 5 | 5 | 5 | 5 |
| 37 | 400 | 5 | 5 | 5 | 5 | 5 | 5 |
| 38 | 400 | 5 | 5 | 5 | 5 | 5 | 5 |
| 39 | 400 | 5 | 5 | 5 | 5 | 5 | 5 |
| 40 | 400 | 5 | 5 | 5 | 5 | 5 | 5 |
| 41 | 400 | 5 | 5 | 5 | 5 | 5 | 5 |
| 42 | 400 | 5 | 5 | 5 | 5 | 5 | 4 |
| 43 | 400 | 5 | 5 | 5 | 5 | 5 | 5 |
| 44 | 400 | 5 | 5 | 5 | 5 | 5 | 5 |
| 45 | 400 | 5 | 5 | 5 | 5 | 5 | 5 |
| 46 | 400 | 5 | 5 | 5 | 5 | 5 | 5 |
| 47 | 400 | 5 | 5 | 5 | 5 | 5 | 5 |
| 48 | 400 | 5 | 5 | 5 | 5 | 5 | 5 |
| 49 | 400 | 5 | 5 | 5 | 5 | 5 | 5 |
| 50 | 400 | 5 | 5 | 5 | 5 | 5 | 5 |
| 51 | 400 | 5 | 5 | 5 | 5 | 5 | 5 |
| 52 | 400 | 5 | 5 | 5 | 5 | 5 | 5 |
| 53 | 400 | 5 | 5 | 5 | 5 | 5 | 5 |
| 54 | 400 | 5 | 5 | 5 | 5 | 5 | 5 |
| 55 | 400 | 5 | 5 | 5 | 5 | 5 | 5 |
| 56 | 400 | 5 | 5 | 5 | 5 | 5 | 5 |
| Comparative Compound A | 400 | 0 | 1 | 2 | 1 | 0 | 4 |
| Comparative Compound B | 400 | 0 | 1 | 2 | 1 | 0 | 5 |
| Comparative Compound C | 400 | 1 | 0 | 1 | 0 | 0 | 1 |

TABLE 3-c

| Compound No. | Dose of active ingredient (g/10 a) | Herbicidal effects | | | | | |
| --- | --- | --- | --- | --- | --- | --- | --- |
| | | Ech | Dig | Pol | Ama | Che | Cyi |
| 57 | 400 | 5 | 5 | 5 | 5 | 5 | 5 |
| 58 | 400 | 5 | 5 | 5 | 5 | 5 | 5 |
| 59 | 400 | 5 | 5 | 5 | 5 | 5 | 5 |
| 60 | 400 | 5 | 5 | 5 | 5 | 5 | 5 |
| 61 | 400 | 5 | 5 | 4 | 5 | 5 | 5 |
| 62 | 400 | 5 | 5 | 5 | 5 | 5 | 5 |
| 63 | 400 | 5 | 5 | 5 | 5 | 5 | 5 |

TABLE 3-c-continued

| | | | | | | | |
|---|---|---|---|---|---|---|---|
| 64 | 400 | 5 | 5 | 5 | 4 | 5 | 3 |
| 65 | 400 | 4 | 5 | 5 | 4 | 5 | 4 |
| 66 | 400 | 5 | 5 | 5 | 5 | 5 | 4 |
| 67 | 400 | 5 | 5 | 5 | 5 | 5 | 4 |
| 68 | 400 | 4 | 5 | 5 | 5 | 5 | 5 |
| 69 | 400 | 5 | 5 | 4 | 4 | 5 | 5 |
| 70 | 400 | 5 | 5 | 5 | 5 | 5 | 4 |
| 71 | 400 | 4 | 5 | 5 | 5 | 5 | 4 |
| 72 | 400 | 5 | 5 | 5 | 5 | 5 | 4 |
| 73 | 400 | 5 | 5 | 5 | 5 | 5 | 5 |
| 74 | 400 | 5 | 5 | 5 | 5 | 5 | 5 |
| 75 | 400 | 4 | 5 | 4 | 4 | 3 | 5 |
| 76 | 400 | 4 | 4 | 4 | 4 | 5 | 4 |
| 77 | 400 | 5 | 5 | 5 | 5 | 5 | 5 |
| Comparative | | | | | | | |
| Compound A | 400 | 0 | 0 | 1 | 2 | 0 | 4 |
| Compound B | 400 | 0 | 1 | 2 | 1 | 1 | 4 |
| Compound C | 400 | 1 | 1 | 1 | 0 | 0 | 1 |

Note 1. The abbreviations of the tested plants are as follows (the same abbreviations may be used in other tables):
Ech: barnyardgrass (*Echinochloa crus-galli*)
Dig: crabgrass (*Digitaria sanguinalis*)
Pol: smartweed (*Polygonum lapathifolium*)
Ama: slender amarauth (*Amarathus viridis*)
Che: lambsquarters (*Chenopodium album*)
Cyi: rice flatsedge (*Cyperus iria*)

Note 2. Comparative Compounds A, B and C will be identified below (the same applies in other Tables):
Comparative Compound A (disclosed in Japanese Unexamined Patent Publication No. 55729/1979)

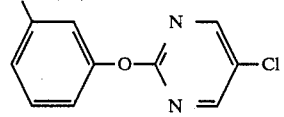

Comparative Compound B (disclosed in Japanese Unexamined Patent Publication No. 55729/1979)

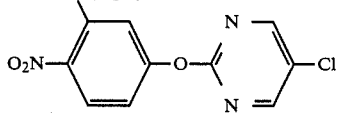

Comparative Compound C (disclosed in Arg. Biol. Chem., Vol. 30, No. 9. 896 (1966))

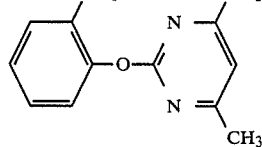

TEST EXAMPLE 2 (Soil treatment)

In a 600 cm² pot filled with soil, seeds of barnyardgrass, crabgrass, smartweed, slender amarauth, lambsquarters and rice flatsedge, were sown, and covered with soil of a thickness of from 0.5 to 1 cm. Two days after the seeding, a predetermined amount of a wettable powder prepared in accordance with Formulation Example 1, was diluted with water and applied to the soil surface at a rate of 100 liters per 10 ares. The evaluation was conducted on the 20th day after the treatment with the herbicide. The results were evaluated in accordance with the standards as identified in Table 2 and shown by the index numbers in Table 4a to 4c.

TABLE 4-a

| Compound No. | Dose of active ingredient (g/10a) | Ech | Dig | Pol | Ama | Che | Cyi |
|---|---|---|---|---|---|---|---|
| 1 | 400 | 5 | 5 | 4 | 5 | 4 | 5 |
| 2 | 400 | 5 | 5 | 5 | 5 | 5 | 5 |
| 3 | 400 | 5 | 5 | 5 | 5 | 5 | 5 |
| 4 | 400 | 1 | 3 | 2 | 5 | 3 | 4 |
| 5 | 400 | 5 | 5 | 5 | 5 | 5 | 5 |
| 6 | 400 | 4 | 4 | 5 | 5 | 5 | 5 |
| 7 | 400 | 3 | 3 | 4 | 5 | 5 | 5 |
| 9 | 400 | 0 | 3 | 4 | 5 | 5 | 5 |
| 13 | 400 | 4 | 5 | 5 | 5 | 5 | 5 |
| 17 | 400 | 2 | 2 | 4 | 4 | 3 | 5 |
| 18 | 400 | 2 | 3 | 4 | 5 | 2 | 2 |
| Comparative Compound A | 400 | 0 | 0 | 0 | 0 | 0 | 5 |
| Comparative Compound B | 400 | 0 | 0 | 0 | 0 | 2 | 5 |
| Comparative Compound C | 400 | 0 | 0 | 0 | 0 | 0 | 0 |

TABLE 4-b

| Compound No. | Dose of active ingredient (g/10 a) | Ech | Dig | Pol | Ama | Che | Cyi |
|---|---|---|---|---|---|---|---|
| 20 | 400 | 0 | 2 | 5 | 5 | 4 | 4 |
| 21 | 400 | 4 | 3 | 4 | 5 | 4 | 3 |
| 22 | 400 | 5 | 5 | 5 | 5 | 5 | 5 |
| 23 | 400 | 5 | 4 | 5 | 5 | 5 | 5 |
| 24 | 400 | 5 | 3 | 4 | 5 | 5 | 5 |
| 25 | 400 | 4 | 3 | 5 | 5 | 5 | 5 |
| 26 | 400 | 0 | 1 | 4 | 5 | 5 | 3 |
| 27 | 400 | 0 | 2 | 5 | 5 | 4 | 4 |
| 28 | 400 | 4 | 3 | 4 | 5 | 5 | 2 |
| 29 | 400 | 5 | 3 | 5 | 5 | 5 | 3 |
| 30 | 400 | 2 | 3 | 5 | 5 | 4 | 3 |
| 31 | 400 | 2 | 3 | 2 | 5 | 5 | 1 |
| 32 | 400 | 0 | 3 | 5 | 5 | 3 | 5 |
| 33 | 400 | 3 | 2 | 5 | 4 | 4 | 2 |
| 34 | 400 | 5 | 5 | 5 | 5 | 5 | 5 |
| 35 | 400 | 5 | 5 | 5 | 5 | 5 | 5 |
| 36 | 400 | 4 | 4 | 5 | 5 | 4 | 4 |
| 37 | 400 | 2 | 3 | 3 | 5 | 4 | 3 |
| 38 | 400 | 2 | 2 | 1 | 5 | 3 | 1 |
| 39 | 400 | 3 | 2 | 4 | 5 | 4 | 3 |
| 40 | 400 | 0 | 1 | 5 | 5 | 3 | 2 |
| 41 | 400 | 4 | 2 | 2 | 5 | 5 | 2 |
| 42 | 400 | 2 | 4 | 5 | 5 | 5 | 4 |
| 43 | 400 | 3 | 3 | 5 | 5 | 3 | 0 |
| 44 | 400 | 0 | 2 | 3 | 5 | 2 | 4 |
| 45 | 400 | 1 | 2 | 1 | 5 | 4 | 4 |
| 46 | 400 | 0 | 2 | 5 | 5 | 5 | 2 |
| 47 | 400 | 2 | 4 | 3 | 5 | 4 | 5 |
| 48 | 400 | 0 | 3 | 5 | 5 | 4 | 3 |
| 49 | 400 | 5 | 5 | 5 | 5 | 4 | 5 |
| 50 | 400 | 3 | 3 | 5 | 5 | 4 | 5 |
| 51 | 400 | 4 | 4 | 5 | 5 | 5 | 5 |
| 52 | 400 | 4 | 5 | 4 | 5 | 4 | 5 |
| Comparative Compound A | 400 | 0 | 0 | 0 | 0 | 0 | 4 |
| Comparative Compound B | 400 | 0 | 0 | 0 | 0 | 0 | 4 |
| Comparative Compound C | 400 | 0 | 0 | 0 | 0 | 0 | 0 |

TABLE 4-c

| Compound No. | Dose of active ingredient (g/10 a) | Herbicidal effects ||||||
|---|---|---|---|---|---|---|---|
| | | Ech | Dig | Pol | Ama | Che | Cyi |
| 59 | 400 | 1 | 4 | 5 | 5 | 4 | 3 |
| 60 | 400 | 2 | 4 | 1 | 4 | 5 | 5 |
| 62 | 400 | 5 | 5 | 5 | 5 | 5 | 5 |
| 63 | 400 | 4 | 5 | 5 | 5 | 5 | 5 |
| 64 | 400 | 3 | 3 | 3 | 4 | 4 | 5 |
| 65 | 400 | 5 | 5 | 4 | 5 | 5 | 5 |
| 66 | 400 | 5 | 5 | 4 | 5 | 5 | 5 |
| 67 | 400 | 5 | 5 | 5 | 5 | 5 | 5 |
| 68 | 400 | 5 | 5 | 5 | 5 | 5 | 5 |
| 69 | 400 | 5 | 5 | 5 | 5 | 5 | 5 |
| 70 | 400 | 5 | 5 | 4 | 5 | 5 | 5 |
| 71 | 400 | 4 | 5 | 4 | 5 | 5 | 5 |
| 75 | 400 | 2 | 2 | 1 | 2 | 3 | 1 |
| 76 | 400 | 4 | 5 | 3 | 5 | 5 | 3 |
| 77 | 400 | 1 | 1 | 2 | 5 | 3 | 1 |
| Comparative Compound A | 400 | 0 | 0 | 0 | 0 | 0 | 4 |
| Comparative Compound B | 400 | 0 | 0 | 0 | 0 | 1 | 4 |
| Comparative Compound C | 400 | 0 | 0 | 0 | 0 | 0 | 0 |

TEST EXAMPLE 3 (selectivity test)

In a 600 cm² pot filled with soil, seeds of barnyardgrass, proso millet, crabgrass, greenfoxtail, shattercane, smartweed and common cocklebur and corn and rhizomes of johnsongrass were sown or planted, and cultured in a greenhouse until corn grew to 3 to 4 leaf stage. A predetermined amount of a wettable powder prepared in accordance with Formulation Example 1, was diluted with water and applied to the foliage of the grown weeds and crop plant at a rate of 100 liters per 10 ares. The herbicidal effects were evaluated in accordance with the standards as identified in Table 2, and the phytotoxicity was evaluated in accordance with the standards as identified in Table 5, on the 30th day after the treatment with the herbicide. The results are shown in Table 6a, 6b and 6c.

TABLE 5

| Index | Phytotoxicity |
|---|---|
| 0 | No phytotoxicity |
| 1 | Phytotoxicity more than 0% and less than 30% |
| 2 | Phytotoxicity at least 30% and less than 50% |
| 3 | Phytotoxicity at least 50% and less than 70% |
| 4 | Phytotoxicity at least 70% and less than 90% |
| 5 | Phytotoxicity at least 90% to completely withered |

TABLE 6-a

| Compound No. | Dose of active ingredient (g/10 a) | Herbicidal effects |||||||  | Phytotoxicity |
|---|---|---|---|---|---|---|---|---|---|
| | | Ech | Dig | Set | Sob | Pol | Xan | Soh | Zea |
| 1 | 25 | 5 | 5 | 5 | 5 | 5 | 4 | 5 | 0 |
| 2 | 25 | 5 | 5 | 5 | 5 | 5 | 3 | 5 | 0 |
| 3 | 25 | 4 | 4 | 5 | 5 | 5 | 3 | 5 | 0 |
| 6 | 25 | 5 | 5 | 5 | 5 | 5 | 4 | 5 | 0 |
| 7 | 25 | 5 | 5 | 5 | 5 | 5 | 5 | 5 | 2 |
| 8 | 25 | 5 | 4 | 5 | 5 | 5 | 2 | 5 | 0 |
| 9 | 25 | 5 | 5 | 5 | 5 | 5 | 2 | 5 | 0 |
| 11 | 25 | 5 | 5 | 5 | 5 | 5 | 2 | 5 | 0 |
| 12 | 25 | 5 | 4 | 4 | 5 | 5 | 2 | 5 | 0 |
| 13 | 25 | 4 | 4 | 3 | 4 | 3 | 2 | 3 | 0 |
| 19 | 25 | 5 | 3 | 5 | 5 | 3 | 1 | 2 | 0 |
| Comparative-compound A | 25 | 0 | 0 | 0 | 0 | 0 | 0 | 0 | 0 |
| Comparative-compound D | 25 | 0 | 0 | 0 | 1 | 0 | 0 | 0 | 0 |

TABLE 6-b

| Compound No. | Dose of active ingredient (g/10 a) | Herbicidal effect ||||  | Phytotoxicity |
|---|---|---|---|---|---|---|
| | | Set | Sob | Pam | Soh | Zea |
| 20 | 25 | 5 | 5 | 5 | 5 | 0 |
| 21 | 25 | 5 | 5 | 5 | 5 | 2 |
| 22 | 25 | 5 | 5 | 4 | 5 | 1 |
| 23 | 25 | 5 | 5 | 5 | 5 | 0 |
| 24 | 25 | 5 | 5 | 5 | 5 | 1 |
| 25 | 25 | 5 | 5 | 5 | 5 | 0 |
| 26 | 25 | 5 | 5 | 4 | 5 | 0 |
| 27 | 25 | 2 | 5 | 2 | 5 | 0 |
| 28 | 25 | 5 | 5 | 5 | 5 | 0 |
| 29 | 25 | 5 | 5 | 2 | 5 | 0 |
| 30 | 25 | 5 | 5 | 5 | 5 | 2 |
| 31 | 25 | 5 | 5 | 2 | 5 | 0 |
| 32 | 25 | 5 | 5 | 3 | 4 | 0 |
| 33 | 25 | 5 | 5 | 5 | 5 | 1 |
| 34 | 25 | 5 | 5 | 5 | 5 | 0 |
| 35 | 25 | 5 | 5 | 5 | 5 | 1 |
| 36 | 25 | 2 | 5 | 2 | 5 | 0 |
| 37 | 25 | 5 | 5 | 5 | 5 | 0 |
| 38 | 25 | 3 | 5 | 3 | 4 | 0 |
| 41 | 25 | 5 | 5 | 4 | 5 | 0 |
| 42 | 25 | 4 | 3 | 5 | 3 | 0 |
| 43 | 25 | 5 | 5 | 5 | 5 | 0 |
| 44 | 25 | 5 | 5 | 5 | 5 | 0 |
| 46 | 25 | 5 | 5 | 5 | 5 | 0 |
| 47 | 25 | 5 | 5 | 5 | 5 | 0 |
| 49 | 25 | 5 | 5 | 5 | 5 | 3 |
| 50 | 25 | 5 | 5 | 1 | 5 | 0 |
| 51 | 25 | 4 | 5 | 4 | 5 | 0 |
| 52 | 25 | 5 | 5 | 5 | 5 | 3 |
| Comparative Compound A | 25 | 0 | 0 | 0 | 0 | 0 |
| Comparative Compound B | 25 | 0 | 1 | 0 | 0 | 0 |

TABLE 6-c

| Compound No. | Dose of active ingredient (g/10 a) | Herbicidal effect ||||  | Phytotoxicity |
|---|---|---|---|---|---|---|
| | | Set | Sob | Pam | Soh | Zea |
| 59 | 20 | 5 | 5 | 5 | 4 | 1 |

TABLE 6-c-continued

| Compound No. | Dose of active ingredient (g/10 a) | Herbicidal effect | | | | Phytotoxicity |
|---|---|---|---|---|---|---|
| | | Set | Sob | Pam | Soh | Zea |
| 60 | 20 | 5 | 5 | 5 | 5 | 2 |
| 62 | 20 | 5 | 5 | 5 | 5 | 1 |
| 63 | 20 | 5 | 5 | 5 | 5 | 1 |
| 65 | 20 | 4 | 5 | 1 | 4 | 0 |
| 66 | 20 | 5 | 5 | 2 | 5 | 0 |
| 67 | 20 | 5 | 4 | 2 | 4 | 0 |
| 68 | 20 | 5 | 5 | 3 | 5 | 0 |
| 69 | 20 | 5 | 5 | 4 | 5 | 0 |
| 70 | 20 | 5 | 5 | 3 | 5 | 0 |
| 71 | 20 | 5 | 5 | 1 | 3 | 0 |
| 77 | 20 | 1 | 5 | 1 | 2 | 0 |
| Comparative Compound A | 20 | 0 | 0 | 0 | 0 | 0 |
| Comparative Compound B | 20 | 0 | 0 | 0 | 0 | 0 |

Note 1. Abbreviations for the tested plants are as follows.
Ech: barnyardgrass (*Echinochloa crus-galli*)
Dig: crabgrass (*Digitaria sanguinalis*)
Set: greenfoxtail (*Setaria viridis*)
Sob: shattercane (*Sorghum bicolor*)
Pam: proso millet (*Panicum millaceum*)
Pol: smartweed (*Polygonum lapathifolium*)
Xan: common cocklebur (*Xanthium strumarium*)
Soh: johnsongrass (*Sorghum halepense*)
Zea: corn (*Zea mays*)

We claim:

1. A picolinic acid compound having herbicidal activity and having the formula:

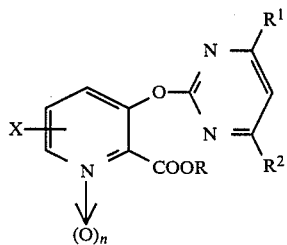

wherein R is a hydrogen atom, an alkyl group, an alkenyl group, an alkynyl group, an alkali metal atom, an alkaline earth metal atom, an alkylammonium group or

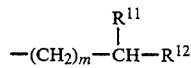

[wherein $R^{11}$ is a hydrogen atom or an alkyl group, $R^{12}$ is an alkoxycarbonyl group, a cyano group, a halogen atom, an acetyl group, a pivaloyl group, a benzoyl group, an alkoxy group, a phenoxy group, a halogenoacetyloxy group, a methylsulfonyloxy group, a hydroxyl group, an alkylthio group, an alkylsulfonyl group, a phenylthio group, a dialkylamino group, a naphthyl group, a pyridyl group,

(wherein W is a hydrogen atom, a halogen atom, an alkyl group, an alkoxy group, a phenoxy group, a nitro group or an alkoxycarbonyl group, and e is 1 or 2) or

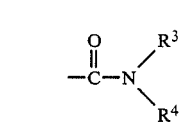

(wherein each of $R^3$ and $R^4$ which may be the same or different, is a hydrogen atom, an alkyl group, an alkenyl group or a phenyl group), and m is an integer of from 0 to 2 ], each of $R^1$ and $R^2$ which may be the same or different, is a halogen atom, a lower alkyl group, a lower alkoxy group or a lower haloalkoxy group, X is a hydrogen atom, a halogen atom or a lower alkyl group, and n is 0 or 1, or a salt thereof.

2. The picolinic acid compound according to claim 1, wherein n is 0.

3. The picolinic acid compound according to claim 2, wherein X is a hydrogen atom.

4. The picolinic acid compound according to claim 3, wherein each of $R^1$ and $R^2$ is a lower alkoxy group.

5. The picolinic acid compound according to claim 4, wherein each of $R^1$ and $R^2$ is a methoxy group.

6. The picolinic acid compound according to claim 1, 4 or 5, wherein R is a hydrogen atom, a $C_1$-$C_5$ alkyl group, an unsaturated benzyl group, a halogen-substituted benzyl group, a lower alkyl-substituted benzyl group, an alkenyl group, an alkynyl group, a phenethyl group, a methylthiomethyl group, an alkali metal atom or an alkylammonium group.

7. The picolinic acid compound according to claim 1, 4 or 5, wherein R is a hydrogen atom, a $C_1$-$C_4$ alkyl group, a propenyl group, a propynyl group, a chlorobenzyl group, a phenethyl group or a methylthiomethyl group, an alkali metal atom or an alkylammonium group.

8. The picolinic acid compound according to claim 1, which is methyl 3-(4,6-dimethoxypyrimidin-2-yl)oxy picolinate, n-butyl 3-(4,6-dimethoxypyrimidin-2-yl)oxy picolinate, 2'-propenyl 3-(4,6-dimethoxypyrimidin-2-yl)oxy picolinate, 3-(4,6-dimethoxypyrimidin-2-yl)oxy picolinic acid, 2'-propynyl 3-(4,6-dimethoxypyrimidin-2-yl)oxy pycolinate, 4'-chlorobenzyl 3-(4,6-dimethoxypyrimidin-2-yl)oxy picolinate, 3'-chlorobenzyl 3-(4,6-dimethoxypyrimidin-2-yl)oxy picolinate, 2'-chlorobenzyl 3-(4,6-dimethoxypyrimidin-2-yl)oxy picolinate, phenethyl 3-(4,6-dimethoxypyrimidin-2-yl)oxy picolinate, methylthiomethyl 3-(4,6-dimethoxypyrimidin-2-yl)oxy picolinate, sodium 3-(4,6-dimethoxypyrimidin-2-yl)oxy picolinate or isopropyl ammonium 3-(4,6-dimethoxypyrimidin-2-yl)oxy picolinate.

9. A herbicidal composition comprising a herbicidally effective amount of a picolinic acid compound or a salt thereof as defined in claim 1 and an agricultural adjuvant.

10. A method for killing weeds which comprises applying a herbicidally effective amount of a picolinic acid compound or a salt thereof as defined in claim 1 to a locus to be protected.

11. A picolinic acid compound having the formula:

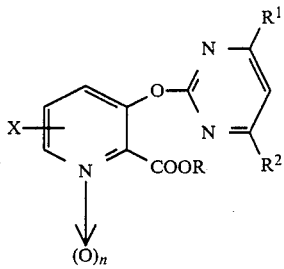

wherein R is hydrogen, alkyl, lower alkenyl, lower alkynyl, an alkali metal atom, an alkaline earth metal atom, lower alkyl ammonium, or

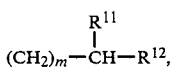

wherein $R^{11}$ is a hydrogen atom or lower alkyl; $R^{12}$ is lower alkoxycarbonyl, cyano, halogen, acetyl, pivaloyl, benzoyl, lower alkoxy, phenoxy, halogenoacetyloxy, methylsulfonyloxy, hydroxyl, lower alkylthio, lower alkylsulfonyl, phenylthio, lower dimethylamino, naphthyl, pyridyl,

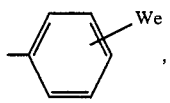

wherein W is hydrogen, halogen, alkyl, lower alkoxy, phenoxy, nitro, or alkoxycarbonyl and e is 1 or 2, or

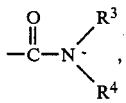

wherein each of $R^3$ and $R^4$, which may be the same or different, is hydrogen, lower alkyl, lower alkenyl, or phenyl; and m is 0, 1 or 2, each of $R^1$ and $R^2$, which may be the same or different, is halogen, lower alkyl, lower alkoxy or lower haloalkoxy, X is hydrogen, halogen or lower alkyl, and n is 0 or 1, or a salt thereof.

12. The picolinic acid compound according to claim 11, wherein n is 0.

13. The picolinic acid compound according to claim 12, wherein X is a hydrogen atom.

14. The picolinic acid compound according to claim 13, wherein each of $R^1$ and $R^2$ is a lower alkoxy group.

15. The picolinic acid compound according to claim 14, wherein each of $R^1$ and $R^2$ is a methoxy group.

16. The picolinic acid compound according to claims 11, 14 or 15, wherein R is a hydrogen atom, a $C_1$-$C_5$ alkyl group, an unsaturated benzyl group, a halogen-substituted benzyl group, a lower alkyl-substituted benzyl group, an alkenyl group, an alkynyl group, a phenethyl group, a methylthiomethyl group, an alkali metal atom, an alkaline earth metal atom, or an alkylammonium group.

17. The picolinic acid compound according to claims 11, 14 or 15, wherein R is a hydrogen atom, a $C_1$-$C_4$ alkyl group, a propenyl group, a propynyl group, a chlorobenzyl group, a phenethyl group or a methylthiomethyl group, an alkali metal atom, an alkaline earth metal atom, or an alkylammonium group.

18. A herbicidal composition comprising a herbicidally effective amount of a picolinic acid compound or a salt thereof as defined in claim 11 and an agricultural adjuvant.

19. A method for killing weeds which comprises applying a herbicidally effective amount of a picolinic acid derivative or a salt thereof as defined in claim 11 to a locus to be protected.

20. Methyl 3-(4,6-dimethoxypyrimidin-2-yl)oxy picolinate.

21. n-Butyl 3-(4,6-dimethoxypyrimidin-2-yl)oxy picolinate.

22. 2'-Propenyl 3-(4,6-dimethoxypyrimidin-2-yl)oxy picolinate.

23. 3-(4,6-dimethoxypyrimidin-2-yl)oxy picolinic acid.

24. 2'-Propynyl 3-(4,6-dimethoxypyrimidin-2-yl)oxy picolinate.

25. 4'-Chlorobenzyl 3-(4,6-dimethoxypyrimidin-2-yl)oxy picolinate.

26. 3'-Chlorobenzyl 3-(4,6-dimethoxypyrimidin-2-yl)oxy picolinate.

27. 2'-Chlorobenzyl 3-(4,6-dimethoxypyrimidin-2-yl)oxy picolinate.

28. Phenethyl 3-(4,6-dimethoxypyrimidin-2-yl)oxy picolinate.

29. Methylthiomethyl 3-(4,6-dimethoxypyrimidin-2-yl)oxy picolinate.

30. Sodium 3-(4,6-dimethoxypyrimidin-2-yl)oxy picolinate.

31. Isopropyl ammonium 3-(4,6-dimethoxypyrimidin-2-yl)oxy picolinate.

32. Ethyl 3-(4,6-dimethoxypyrimidin-2-yl)oxy picolinate.

33. n-Propyl 3-(4,6-dimethoxypyrimidin-2-yl)oxy picolinate.

34. Isopropyl 3-(4,6-dimethoxypyrimidin-2-yl)oxy picolinate.

35. A picolinic acid compound having the formula:

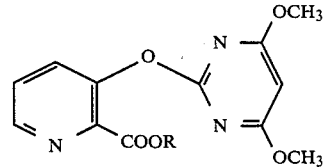

wherein R is hydrogen or $C_{1-5}$ alkyl or a salt thereof.

* * * * *

UNITED STATES PATENT AND TRADEMARK OFFICE
CERTIFICATE OF CORRECTION

PATENT NO. : 4,832,729
DATED : MAY 23, 1989
INVENTOR(S) : MASAHIRO SHIGEMATSU ET AL

It is certified that error appears in the above-identified patent and that said Letters Patent is hereby corrected as shown below:

Delete the formula in the heading of Table 1 as it appears at the tops of columns 5 and 6, 7 and 8, 9 and 10, 11 and 12, 13 and 14, 15 and 16 in favor of the following formula:

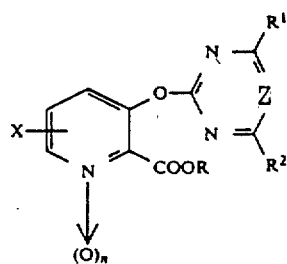

Signed and Sealed this

Twenty-third Day of October, 1990

Attest:

HARRY F. MANBECK, JR.

Attesting Officer    Commissioner of Patents and Trademarks